United States Patent [19]

North et al.

[11] Patent Number: 5,006,544

[45] Date of Patent: Apr. 9, 1991

[54] IMIDAZOLE DERIVATIVES AND PHARMACEUTICAL USE THEREOF

[75] Inventors: Peter C. North, Hertfordshire; David J. Cavalla, Cambridge; Derek J. M. Black, Hertfordshire, all of England

[73] Assignee: Glaxo Group Limited, England

[21] Appl. No.: 420,324

[22] Filed: Oct. 12, 1989

[30] Foreign Application Priority Data

Oct. 13, 1988 [GB] United Kingdom ............... 8823980

[51] Int. Cl.$^5$ ............... C07D 405/06; C07D 409/06; A61K 31/415
[52] U.S. Cl. ..................................... 514/385; 548/336
[58] Field of Search ......................... 548/336; 514/385

[56] References Cited

U.S. PATENT DOCUMENTS

| 4,626,988 | 4/1981 | Widdig et al. | |
| 4,808,581 | 2/1989 | Oxford et al. | 548/336 |
| 4,859,662 | 8/1989 | Coates et al. | 548/336 |
| 4,918,080 | 5/1990 | Oxford . | |

FOREIGN PATENT DOCUMENTS

| 248420 | 12/1987 | European Pat. Off. . |
| 291172 | 11/1988 | European Pat. Off. . |
| 242973 | 10/1989 | European Pat. Off. . |
| 336759 | 10/1989 | European Pat. Off. . |
| 3740352 | 6/1988 | Fed. Rep. of Germany . |
| 2106509 | 4/1983 | United Kingdom . |

Primary Examiner—David B. Springer
Attorney, Agent, or Firm—Bacon & Thomas

[57] ABSTRACT

The invention provides imidazole derivatives of the general formula (I)

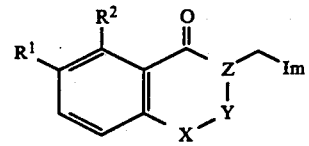

(I)

wherein Im representes an imidazolyl group of the formula:

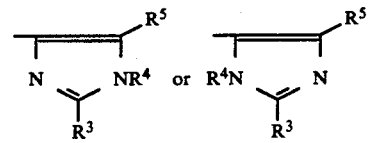

and one of the groups represented by $R^3$, $R^4$ and $R^5$ is a hydrogen atom, or a $C_{1-6}$alkyl, $C_{3-7}$cycoalkyl, $C_{3-6}$alkenyl, phenyl or phenyl$C_{1-3}$alkyl group, and each of the other two groups, which may be the same or different, represents a hydrogen atom or a $C_{1-6}$alkyl group;

$R^1$ and $R^2$ each represent a hydrogen atom, or together with the carbon atoms to which they are attached form a phenyl ring;

X represents an oxygen or a sulphur atom, or a group $NR^6$, wherein $R^6$ represents a $C_{1-6}$alkyl group;

Z—Y represents the group $CH$—$CH_2$ or $C$=$CH$;

and physiologically acceptable salts and solvates thereof.

The compounds of formula (I) are potent and selective antagonists of 5-hydroxytryptamine at 5-HT$_3$ receptors and are useful, for example, in the treatment of psychotic disorders, anxiety and nausea and vomiting.

9 Claims, No Drawings

IMIDAZOLE DERIVATIVES AND PHARMACEUTICAL USE THEREOF

This invention relates to imidazole derivatives, to processes for their preparation, to pharmaceutical compositions containing them and to their medical use.

In particular the invention relates to compounds which are potent and selective antagonists of 5-hydroxytryptamine (5-HT) at 5-HT receptors of the type located on terminals of primary afferent nerves. Receptors of this type are now designated as 5-$HT_3$ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

Imidazol-4(and 5)-yl derivatives having antagonist activity at 5-$HT_3$ receptors have been described previously, for example, in European Patent Specification No. 242973A and in German Offenlegungschrift No. 3740352.

We have now found a novel group of compounds which differ in structure from those described previously, and which are potent antagonists of the effect of 5-HT at 5-$HT_3$ receptors.

Thus the present invention provides an imidazole derivative of the general formula (I):

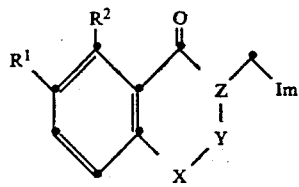

wherein Im represents an imidazolyl group of the formula:

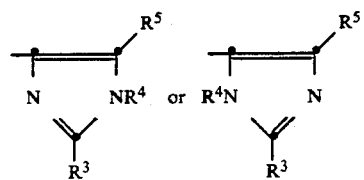

and one of the groups represented by $R^3$, $R^4$ and $R^5$ is a hydrogen atom, or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group;

$R^1$ and $R^2$ each represent a hydrogen atom, or together with the carbon atoms to which they are attached form a phenyl ring;

X represents an oxygen or a sulphur atom, or a group $NR^6$, wherein $R^6$ represents a $C_{1-6}$alkyl group;

Z—Y represents the group CH—$CH_2$ or C≡CH; and physiologically acceptable salts and solvates thereof.

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvates may, for example, be hydrates.

It will be appreciated that when Z—Y represents CH—$CH_2$, the carbon atom to which the group —$CH_2$Im is attached is asymmetric and may exist in the R— or S— configuration. Furthermore, depending on the nature of the substituents $R^3$, $R^4$, $R^5$ and $R^6$, centres of optical and/or geometric isomerism may occur elsewhere in the molecule. All optical isomers of compounds of general formula (I) and their mixtures including the racemic mixtures thereof, and all the geometric isomers of compounds of formula (I), are embraced by the invention.

Referring to the general formula (I), the alkyl groups represented by $R^3$, $R^4$, $R^5$ and $R^6$ may be straight chain or branched chain alkyl groups, for example, methyl, ethyl, propyl, prop-2-yl, butyl, but-2-yl, 2-methylprop-2-yl, pentyl, pent-3-yl or hexyl. An alkenyl group may be, for example, a prop-2-enyl group. When $R^4$ represents a $C_{3-6}$alkenyl group, the double bond may not be adjacent to the nitrogen atom. A phenyl$C_{1-3}$alkyl group may be, for example, a benzyl group. A cycloalkyl group may be, for example, a cyclopentyl group.

A preferred class of compounds of formula (I) is that in which $R^3$, $R^4$ and $R^5$ each independently represent a hydrogen atom or a $C_{1-4}$alkyl (e.g. methyl) group. A further preferred class of compounds of formula (I) is that in which $R^3$ and $R^4$ each represent a hydrogen atom and $R^5$ represents a $C_{1-4}$alkyl (e.g. methyl) group.

Another preferred class of compounds of formula (I) is that in which X represents an oxygen atom. Within this preferred class of compounds, a further preferred class of compounds is that in which $R^1$ and $R^2$ together with the carbon atoms to which they are attached form a phenyl ring.

A further preferred class of compounds of formula (I) is that in which Z—Y represents the group CH—$CH_2$.

A particularly preferred compound according to the invention is 2,3-dihydro-2-[(5-methyl-1H-imidazol-4-yl)methyl]-1H-naphtho[2,1-b]-pyran-1-one and its physiologically acceptable salts and solvates.

The potent and selective antagonism of 5-HT at 5-$HT_3$ receptors by the compounds of the invention has been demonstrated by their ability to inhibit 3-(5-methyl-1H-imidazol-4-yl)-1-[1-(methyl-$t_3$)-1H-indol-3-yl]-1-propanone binding in rat entorhinal cortex homogenates (following the general procedure described by G. Kilpatrick et al. in *Nature*, 1987, 330, 746), and/or by their ability to inhibit the 5-Ht-induced depolarisation of the rat isolated vagus nerve preparation.

Compounds of formula (I), which antagonise the effect of 5-HT at 5-$HT_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine; obesity and conditions such as bulimia; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome; migraine; obesity and conditions such as bulimia; pain; dependency on drugs or substances of abuse; depression; or dementia or another cognitive disorder, which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates (e.g. hydrates), for use in human or veterinary medicine, and formulated for administration by any convenient route.

Such compositions may be formulated in conventional manner using one or more physiologically acceptable carriers and/or excipients.

Thus the compounds according to the invention may be formulated for oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine, cimetidine, famotidine, nizatidine or roxatidine) or $H+K+ATPase$ inhibitors (e.g. omeprazole). In the treatment of nausea and vomiting, compounds of formula (I) may also be administered in combination with dexamethasone or a cyclo-oxygenase inhibitor such as piroxicam.

A proposed dose of the compounds of the invention for administration to man (of approximately 70 kg body weight) is 0.001 to 100 mg, preferably 0.01 to 50 mg, of the active ingredient per unit dose expressed as the weight of free base, which could be administered, for example, 1 to 4 times per day. It will be appreciated that it may be necessary to make routine variations to the dosage, depending on the age and condition of the patient. The dosage will also depend on the route of administration.

Compounds of general formula (I) and physiologically acceptable salts or solvates thereof may be prepared by the general methods outlined hereinafter. In the following description, the groups $R^1$, $R^2$, X and Im are as defined for compounds of general formula (I) unless otherwise stated.

According to a first general process (A), a compound of formula (I) wherein Z—Y represents the group $CH—CH_2$, may be prepared by hydrogenation of a compound of formula (II):

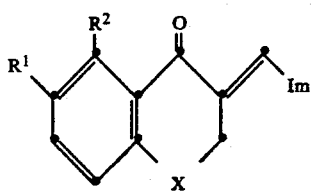

or a protected derivative thereof, followed where necessary by removal of any protecting groups.

Hydrogenation according to general process (A) may be effected using conventional procedures, for example using hydrogen in the presence of a noble metal catalyst (e.g. palladium, Raney nickel, platinum or rhodium). The catalyst may be supported on, for example, charcoal, alumina or alternatively a homogeneous catalyst such as tris(triphenylphosphine)rhodium chloride may be used. The hydrogenation will generally be effected in a solvent such as an alcohol (e.g. methanol or ethanol), an ether (e.g. dioxan), a halogenated hydrocarbon (e.g. dichloromethane) or an ester (e.g. ethyl acetate) or mixtures thereof, and at a temperature in the range $-20°$ to $+100°$ C., preferably $0°$ to $50°$ C.

According to another general process (B), a compound of formula (I) wherein Z—Y represents the group C=CH, may be prepared by reacting a compound of formula (II), or a protected derivative thereof, with an organic acid (e.g. aqueous acetic acid or p-toluenesulphonic acid) or a mineral acid (e.g. hydrochloric acid), followed where necessary by removal of any protecting groups.

According to another general process (C), a compound of general formula (I) may be converted into another compound of formula (I) using conventional techniques. Such conventional techniques include hydrogenation and alkylation using protection and deprotection where necessary.

Thus, according to one embodiment of the interconversion process (C), hydrogenation may be used to convert a compound of formula (I) wherein Z—Y represents the group C=CH into a compound of formula (I) wherein Z—Y represents the group CH—CH$_2$, or to convert an alkenyl into an alkyl substituent. Hydrogenation according to general process (C) may be effected using conventional procedures, for example as described above for general process (A).

The term 'alkylation' according to general process (C) includes the introduction of other groups such as cycloalkyl, alkenyl or phenalkyl groups.

Thus, for example a compound of formula (I) in which $R^6$ represents a $C_{1-6}$alkyl group may be prepared by alkylating a compound of formula (I) in which $R^6$ represents a hydrogen atom, or a compound in which $R^4$ represents a $C_{1-6}$alkyl, $C_{3-7}$cycloalkyl, $C_{3-6}$alkenyl or phenyl$C_{1-3}$alkyl group may be prepared by alkylating the corresponding compound of formula (I) in which $R^4$ represents a hydrogen atom, using conventional procedures, for example as described in published European Patent Specification No. 242973. Thus the reactions may be effected using an appropriate alkylating agent of formula $R^7Z$ (where $R^7$ is the group to be introduced and Z is a leaving atom or group), preferably in the presence of a base.

It should be appreciated that in the above transformations it may be necessary or desirable to protect any sensitive groups in the molecule of the compound in question to avoid undesirable side reactions. For example, it may be necessary to protect the keto group, for example, as a ketal or a thioketal. It may also be necessary to protect the imidazole nitrogen atom, for example with an arylmethyl (e.g. trityl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group.

Thus according to another general process (D), a compound of general formula (I) may be prepared by the removal of any protecting groups from a protected form of a compound of formula (I). Deprotection may be effected using conventional techniques such as those described in 'Protective Groups in Organic Synthesis' by T. W. Greene (John Wiley and Sons, 1981).

For example a ketal such as an alkyleneketal group may be removed by treatment with a mineral acid such as hydrochloric acid. A thioketal group may be cleaved by treatment with a mercuric salt, (e.g. mercuric chloride), in a suitable solvent, such as ethanol. A trityl group may be cleaved by acid hydrolysis (e.g. using dilute hydrochloric or acetic acid). An alkoxyalkyl group may be removed using a mineral acid (e.g. dilute hydrochloric acid). An acyl group may be removed by hydrolysis under acidic or basic conditions (e.g. using hydrogen bromide or sodium hydroxide). A sulphonyl group may also be removed by alkaline or acidic hydrolysis.

Compounds of formula (II) may be prepared by condensing a compound of formula (III):

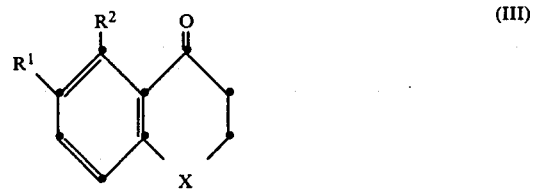

with a compound of formula (IV):

OHC—Im                                              (IV)

or a protected derivative thereof, in the presence of a base such as an alkali metal hydroxide or alkoxide, followed where necessary by removal of any protecting groups.

The reaction may conveniently be effected using an alkali metal hydroxide (e.g. sodium or potassium hydroxide) in an alcohol (e.g. methanol or ethanol) or water, or mixtures thereof, or using an alkali metal alkoxide (e.g. sodium ethoxide or potassium t-butoxide) in the corresponding alcohol (e.g. ethanol or t-butanol) or in an inert solvent such as an ether (e.g. tetrahydrofuran), at a temperature in the range of $0°$ to $100°$ C.

Compounds of formula (III) are either known or may be prepared from known compounds by conventional methods.

Compounds of formula (IV) and protected derivatives thereof may be prepared, for example, by the method described in published European Patent Specification No. 242973A.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compounds of the invention may be obtained by resolution of a mixture of enantiomers (e.g. a racemic mixture) using conventional means, such as an optically active resolving acid; see for example 'Stereochemistry of Carbon Compounds' by E. L. Eliel (McGraw Hill, 1962) and 'Tables of Resolving Agents' by S. H. Wilen.

The methods described above for preparing the compounds of the invention may be used for the introduction of the desired groups at any stage in the stepwise formation of the required compounds, and it will be appreciated that these methods can be combined in different ways in such multi-stage processes. The sequence of the reactions in multi-stage processes should of course be chosen so that the reaction conditions used do not affect groups in the molecule which are desired in the final product.

The invention is further illustrated by the following Intermediates and Examples. All temperatures are in °C. Flash column chromatography (FCC) was carried out on silica (Merck 9385). Solvent System A as used for chromatography denotes dichloromethane:ethanol:0.88 ammonia solution. Organic extracts were dried, where indicated, over magnesium sulphate or sodium sulphate. The following abbreviation is used: THF—tetrahydrofuran.

INTERMEDIATE 1

(E)-2,3-Dihydro-2-[[5-methyl-1-(triphenylmethyl)-1$\underline{H}$-imidazol-4-yl]-methylene]-1$\underline{H}$-naphtho[2,1-b]pyran-1-one A mixture of 2,3-dihydro-1$\underline{H}$-naphtho[2,1-b]pyran-1-one (1.13 g) 5-methyl-1-(triphenylmethyl)-1$\underline{H}$-imidazole-4-carboxaldehyde (2.0 g) and potassium hydroxide (0.5 g) in methanol (25 ml) was heated at 50° for 8 h, and then cooled overnight. The resultant solid was filtered off, and washed with methanol (10 ml) and ether (50 ml) to give the title compound (1.79 g), m.p. 164°-167°.

INTERMEDIATE 2

(E)-2,3-Dihydro-3-[[5-methyl-1-(triphenylmethyl)-1$\underline{H}$-imidazol-4-yl]methylene]-4$\underline{H}$-1-benzopyran-4-one A solution of potassium hydroxide (0.5 g) in methanol (5 ml) was added to a solution of 4-chromanone (0.84 g) and 5-methyl-1-(triphenylmethyl)-1$\underline{H}$-imidazole-4-carboxaldehyde (2 g) in methanol (25 ml) with warming, and the resulting solution was stirred at 50° for 3 h. The resultant precipitate was filtered off, washed with methanol (25 ml) and dried to give the title compound (2.6 g), m.p. 231°-233°.

INTERMEDIATE 3

(E)-2,3-Dihydro-3-[[5-methyl-1-(triphenylmethyl)-1$\underline{H}$-imidazol-4-yl]methylene]-4$\underline{H}$1-benzothiopyran-4-one A solution of potassium hydroxide (0.5 g) in methanol (5 ml) was added to a solution of thiochroman-4-one (0.93 g) and 5-methyl-1-(triphenylmethyl)-1$\underline{H}$-imidazole-4-carboxaldehyde (2 g) in methanol (25 ml), and the resulting solution was stirred at 50° for 3.5 h.

The resultant precipitate was filtered off, washed with methanol (20 ml) and dried to give the title compound (2.1 g), m.p. 225°-226°.

EXAMPLE 1

2,3-Dihydro-2-[(5-methyl-1$\underline{H}$-imidazol-4-yl)methyl]-1$\underline{H}$-naphtho[2,1-b]-pyran-1-one maleate A solution of (E)-2,3-dihydro-2-[[5-methyl-1-(triphenylmethyl)-1$\underline{H}$-imidazol-4-yl]methylene]-1$\underline{H}$-naphtho[2,1-b]pyran-1-one (0.83 g) in acetic acid (10 ml), THF (10 ml) and water (10 ml) was heated at reflux for 45 min. The resulting solution was cooled and added to a stirred pre-reduced suspension of 10% palladium oxide on carbon (50% aqueous paste; 90 mg) in ethanol (30 ml) under hydrogen. Stirring was continued for 1 h, and the suspension was then filtered and evaporated in vacuo. The residual semi-solid was partitioned between ether (75 ml; discarded) and 2N hydrochloric acid (3×25 ml). The combined aqueous layers were basified with 2N sodium hydroxide and extracted into dichloromethane (4×25 ml). The combined, dried organic extracts were evaporated in vacuo to give a solid (0.4 g). This was dissolved in ethanol:dichloromethane (1:1; 15 ml), treated with a solution of maleic acid (166 mg) in ethanol (1 ml), evaporated in vacuo and triturated with dry ether to give the title compound (0.45 g). A portion of this solid (0.35 g) was dissolved in hot ethanol (10 ml), and the resulting solution was filtered. The filtrate was evaporated in vacuo and the residue was triturated with dry ether to give the title compound (0.31 g), m.p. 134°-135°.

Analysis Found: C,64.6; H,4.9; N,6.8; $C_{18}H_{16}N_2O_2.C_4H_4O_4$ requires C,64.7; H,4.9; N,6.9%.

Examples 2 and 3 were prepared in a similar manner to Example 1.

EXAMPLE 2

2,3-Dihydro-3-[(5-methyl-1$\underline{H}$-imidazol-4-yl)methyl]-4$\underline{H}$-1-benzopyran-4-one, compound with maleic acid (E)-2,3-Dihydro-3-[[5-methyl-1-(triphenylmethyl)-1$\underline{H}$-imidazol-4-yl]methylene]-4$\underline{H}$-1-benzopyran-4-one (2.4 g) was deprotected and then hydrogenated to give a solid (1.2 g) which was triturated with absolute ethanol[1] (5 ml) to precipitate a solid (0.45 g). Treatment of a solution of this solid in hot ethanol (10 ml) with maleic acid (107 mg) in ethanol (5 ml), followed by addition of dry ether (15 ml) precipitated the title compound (0.5 g), m.p. 140°-141°.

N.m.r. indicated 0.7 mol maleic acid present.

Analysis Found: C,62.2; H,5.2; N,8.4; $C_{14}H_{14}N_2O_2.0.7C_4H_4O_4$ requires C,62.4; H,5.2; N,8.7%.

Treatment of the mother liquor[1] with maleic acid (180 mg) gave a second crop of the title compound (0.75 g), m.p. 135°-137°.

Analysis Found: C,60.2; H,5.1; N,7.7; $C_{14}H_{14}N_2O_2.C_4H_4O_4$ requires C,60.3; H,5.1; N,7.8%.

EXAMPLE 3

2,3-Dihydro-3-[(5-methyl-1$\underline{H}$-imidazol-4-yl)methyl]-4$\underline{H}$-1-benzothiopyran-4-one, compound with maleic acid (E)-2,3-Dihydro-3-[[5-methyl-1-(triphenylmethyl)-1$\underline{H}$-imidazol-4-yl]methylene]-4$\underline{H}$-1-benzothiopyran-4-one n2.0 g) was deprotected and then hydrogenated to give a solid (0.75 g) which was triturated with a mixture of dry ether and ethyl acetate[1] (2:1; 10 ml) to give a solid (0.7 g). A solution of this solid in hot methanol (30 ml) was treated with maleic acid (315 mg) in methanol (5 ml), and the resulting solution was evaporated in vacuo to leave a gum which was triturated with a mixture of ethanol and ether[2] (1:2; 30 ml) to give the title compound (0.59 g) as a solid, m.p. 132°–135°.

N.m.r. indicated 0.67 mol maleic acid present.

Analysis Found: C,59.7; H,5.0; N,8.2; $C_{14}H_{14}N_2OS.0.67C_4H_4O_4$ requires C,59.6; H,5.0; N,8.3%.

Treatment of the mother liquors[1,2] with maleic acid (200 mg) gave a second crop of the title compound (0.38 g), m.p. 126°–127°.

EXAMPLE 4

1-Methyl-3-[(5-methyl-1H-imidazol-4-yl)methyl]-4(1H)-quinolinone

A suspension of 2,3-dihydro-1-methyl-4(1H)-quinolinone (915 mg) and 5-methyl-1-(triphenylmethyl)-1H-imidazole-4-carboxaldehyde (2.0 g) in methanol (25 ml) was treated with a solution of potassium hydroxide (0.5 g) in methanol (5 ml). The suspension was stirred at room temperature for 44 h and then filtered. The collected solid was heated at reflux in a mixture of acetic acid (6 ml), water (5 ml) and THF (15 ml) for 3 h. The solution was treated cautiously with 8% aqueous sodium bicarbonate (180 ml) and extracted with dichloromethane (3×60 ml). The combined, dried organic extracts were evaporated to give a solid, which was purified by FCC eluting with System A (100:12:1.2) to give the title compound (208 mg), m.p. 110°–113°.

N.m.r. indicated 0.11 mol ethanol present.

Water Analysis Found 1.2% w/w≡0.17 mol H₂O.

Analysis Found: C,69.5; H,6.0; N,15.8; $C_{15}H_{15}N_3O.0.11C_2H_6O.0.17H_2O$ requires C,69.9; H,6.2; N,16.1%.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques. Alternatively the tablets may be sugar coated.

Tablets of other strengths may be prepared by altering the ratio of active ingredient to excipients or the compression weight and using punches to suit.

| Direct Compression Tablet | mg/tablet |
|---|---|
| Active Ingredient | 0.50 |
| Calcium Hydrogen Phosphate BP* | 87.25 |
| Croscarmellose Sodium NF | 1.80 |
| Magnesium Stearate BP | 0.45 |
| Compression weight | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 tablet machine fitted with 5.5 mm, flat bevelled edge punches.

| INJECTION FOR INTRAVENOUS ADMINISTRATION | | |
|---|---|---|
| | mg/ml | |
| Active ingredient | 0.05 | 1.0 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the solution may be sterilised by filtration and filled into sterile ampoules under aseptic conditions. The solution may be packed under an inert atmosphere of nitrogen or other suitable gas.

What is claimed is:

1. A compounds of formula (I)

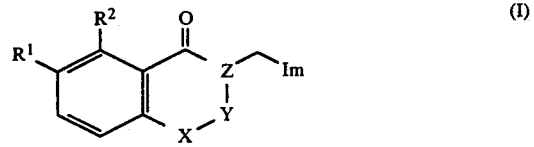

wherein Im represents an imidazolyl group of the formula:

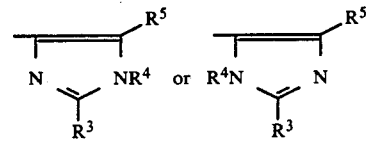

and one of the groups represented by $R^3$, $R^4$ and $R^5$ is a hydrogen atom, or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group;

$R^1$ and $R^2$ each represent a hydrogen atom, or together with the carbon atoms to which they are attached form a phenyl ring;

X represents an oxygen or a sulphur atom;

Z—Y represents the group CH—CH₂ or C≡CH; or a physiologically acceptable salt or hydrate thereof.

2. A compound according to claim 1 in which $R^3$, $R^4$ and $R^5$ each independently represent a hydrogen atom or a $C_{1-4}$alkyl group.

3. A compound according to claim 1 in which $R^3$ and $R^4$ each represent a hydrogen atom and $R^5$ represents a $C_{1-4}$alkyl group.

4. A compound according to claim 1 in which X represents an oxygen atom.

5. A compound according to claim 4 in which $R^1$ and $R^2$ together with the carbon atoms to which they are attached form a phenyl ring.

6. A compound according to claim 1 in which Z—Y represents the group CH—CH₂.

7. 2,3-Dihydro-2-[(5-methyl-1H-imidazol-4-yl)methyl]-1H-naphtho[2,1-b]-pyran-1-one or a physiologically acceptable salt or hydrate thereof.

8. A pharmaceutical composition for treating a condition mediated through 5-HT$_3$ receptors which comprises an effective amount to relieve said condition of at least one compound of formula (I) as defined in claim 1 or a physiologically acceptable salt or hydrate thereof together with at least one physiologically acceptable carrier or excipient.

9. A method of treating a condition mediated through 5-HT$_3$ receptors which comprises administering to a patient an effective amount to relieve said condition of a compound of formula (I) as defined in claim 1 or a physiolgically acceptable salt or hydrate thereof.

* * * * *